(12) United States Patent
Waters et al.

(10) Patent No.: US 8,652,045 B2
(45) Date of Patent: *Feb. 18, 2014

(54) SYSTEM AND METHOD FOR CHARACTERIZING TISSUE BASED UPON HOMOMORPHIC DECONVOLUTION OF BACKSCATTERED ULTRASOUND

(75) Inventors: Kendall R. Waters, Lakewood, OH (US); David L. Goodwin, El Dorado Hills, CA (US)

(73) Assignee: Volcano Corporation, San Diego, CA (US)

( * ) Notice: Subject to any disclaimer, the term of this patent is extended or adjusted under 35 U.S.C. 154(b) by 83 days.

This patent is subject to a terminal disclaimer.

(21) Appl. No.: 13/361,711

(22) Filed: Jan. 30, 2012

(65) Prior Publication Data

US 2012/0130247 A1    May 24, 2012

Related U.S. Application Data

(63) Continuation of application No. 12/129,837, filed on May 30, 2008, now Pat. No. 8,105,237.

(51) Int. Cl.
*A61B 8/00* (2006.01)

(52) U.S. Cl.
USPC .......................................... 600/437; 328/128

(58) Field of Classification Search
USPC ............................ 600/437–469; 382/128–132
See application file for complete search history.

(56) References Cited

U.S. PATENT DOCUMENTS

| | | | |
|---|---|---|---|
| 5,748,491 | A | 5/1998 | Allison et al. |
| 5,776,063 | A | 7/1998 | Dittrich et al. |
| 6,104,670 | A | 8/2000 | Hossack et al. |
| 6,443,895 | B1 | 9/2002 | Adam et al. |
| 7,025,724 | B2 | 4/2006 | Adam et al. |
| 7,074,188 | B2 | 7/2006 | Nair et al. |
| 7,720,268 | B2 | 5/2010 | Slabaugh et al. |
| 2007/0047788 | A1 | 3/2007 | Slablaugh et al. |
| 2007/0083114 | A1 | 4/2007 | Yang et al. |
| 2007/0299343 | A1 | 12/2007 | Waters |

OTHER PUBLICATIONS

International Search Report and Written Opinion dated Jul. 27, 2009 for PCT/US2009/045624.

*Primary Examiner* — Sanjay Cattungal
(74) *Attorney, Agent, or Firm* — Haynes and Boone, LLP

(57) ABSTRACT

A system and method are disclosed that facilitate characterizing vascular plaque tissue based upon spectral analysis of intravascular ultrasound echo signal segments. In particular, a power spectrum analysis of an integrated backscatter parameter renders a set of characterizing parameter values based on received intravascular ultrasound echo signal segments. The resulting parameter values are applied to plaque tissue characterization criteria to render a plaque tissue characterizations for regions of interest. The system and method include computer-executable instructions performed on a computing device to render an estimate of a system transfer function using a homomorphic deconvolution technique.

20 Claims, 12 Drawing Sheets

SYSTEM AND METHOD FOR CHARACTERIZING TISSUE BASED UPON HOMOMORPHIC DECONVOLUTION OF BACKSCATTERED ULTRASOUND

CROSS-REFERENCE TO RELATED APPLICATIONS

This application is a continuation of U.S. patent application Ser. No. 12/129,837 filed on May 30, 2008, now U.S. Pat. No. 8,105,237, which is hereby incorporated by reference in its entirety.

FIELD OF THE INVENTION

The present invention generally relates to the field of imaging systems, and more particularly to intravascular imaging systems and methods for diagnosing vascular disease.

BACKGROUND

The development of new medical technologies has provided an increasing number of options available to doctors for the diagnosis and treatment of cardiovascular diseases. The availability of such equipment has improved the ability of doctors and surgeons to detect and treat cardiovascular disease. Intravascular imaging technologies have enabled doctors to create and view a variety of images generated by a sensor inserted within a vasculature. Such images complement traditional radiological imaging techniques such as angiography by providing images of the tissue within vessel walls rather than showing a two dimensional lumen image.

Intravascular ultrasound (IVUS) analysis finds particular application to a system and method for quantitative component identification within a vascular object including characterization of tissue. It should be appreciated that while the exemplary embodiment is described in terms of an ultrasonic device, or more particularly the use of IVUS data (or a transformation thereof) to characterize a vascular object, the present invention is not so limited. Thus, for example, using backscattered data (or a transformation thereof) based on ultrasound waves or even electromagnetic radiation (e.g., light waves in non-visible ranges) to characterize any tissue type or composition is within the spirit and scope of the present invention.

Imaging portions of a patient's body provides a useful tool in various areas of medical practice for determining the best type and course of treatment. Imaging of the coronary vessels of a patient by techniques involving insertion of a catheter-mounted probe (e.g., an ultrasound transducer array) can provide physicians with valuable information. For example, the image data indicates the extent of a stenosis in a patient, reveals progression of disease, and helps determine whether procedures such as angioplasty or atherectomy are indicated or whether more invasive procedures are warranted.

In an ultrasound imaging system, an ultrasonic transducer probe is attached to a distal end of a catheter that is carefully maneuvered through a patient's body to a point of interest such as within a coronary artery. The transducer probe in known systems comprises a single piezoelectric crystal element that is mechanically scanned or rotated back and forth to cover a sector over a selected angular range. Acoustic signals are transmitted and echoes (or backscatter) from these acoustic signals are received. The backscatter data is used to identify the type or density of a scanned tissue. As the probe is swept through the sector, many acoustic lines (emanating from the probe) are processed to build up a sector-shaped cross-section image of tissue within the patient. After the data is collected, an image of the blood vessel (i.e., an IVUS image) is reconstructed using well-known techniques. This image is then visually analyzed by a cardiologist to assess the vessel components and plaque content. Other known systems acquire ultrasound echo data using a probe comprising an array of transducer elements.

In a particular application of IVUS imaging, ultrasound data is used to characterize tissue within a vasculature and produce images graphically depicting the content of the tissue making up imaged portions of a vessel. Examples of such imaging techniques for performing spectral analysis on ultrasound echoes to render a color-coded tissue map are presented in Nair et al. U.S. Pat. No. 7,074,188 entitled "System and Method of Characterizing Vascular Tissue" and Vince et al. U.S. Pat. No. 6,200,268 entitled "Vascular Plaque Characterization", the contents of which are incorporated herein by reference in their entirety, including any references contained therein. Such systems analyze response characteristics of ultrasound backscatter (reflected sound wave) data to identify a variety of tissue types found in partially occluded vessels including: fibrous tissue, fibro-fatty, necrotic core, and dense calcium. An example of a known plaque characterization imaging technique is referred to as "virtual histology" (VH).

When characterizing the response of tissue that has been subjected to ultrasound waves, parameter values are considered at a data point in an imaged field. Based upon response characteristics (e.g., power spectra) of known tissue types, tissue at the data point is assigned to a particular tissue type (e.g. necrotic core). Known systems utilize an integrated backscatter parameter that represents a power response over a frequency band. The integrated backscatter parameter generally represents a measure of total reflected ultrasound power at a particular point within a vasculature over a specified frequency band.

Furthermore, tissue characterization based on integrated backscatter spectral analysis using an IVUS probe-based system generally includes estimating a system transfer function (i.e., spectral content) so that the portion of a recorded signal attributable to system and catheter components (as opposed to the actual backscatter signal from the imaged field within a body) can be removed from IVUS echo signals initially received and recorded by the IVUS system.

Typically, the system transfer function is determined by performing a reference measurement. The reference measurement characterizes the system and catheter signal properties using an appropriate medium such as a specular reflector glass plate. The transfer function is thereafter applied to received image signals to render the bare image signal (with the system signal effects removed).

In some instances, generating a transfer function based on a reference backscatter medium is impractical or not feasible. As a consequence, image signal processing techniques have been developed for spectral analysis-based tissue characterization systems that do not rely on the aforementioned "reference" measurements. Instead, an estimation of a transfer function for a system is rendered based upon blind deconvolution (BDC). As the name suggests, a user is not aware of the actual system transfer function. An example of a known BDC technique is referred to as "iterated window maximization" (IWM).

Homomorphic deconvolution (HDC) has been proposed for purposes of improving spatial resolution in grayscale ultrasound images and has been discussed in U.S. Pat. Nos. 6,443,895 and 7,025,724. Another HDC algorithm is described by Torfinn Taxt in IEEE Ultrasonics, Ferroelectrics, and Frequency Control, Vol. 53, issue 8, pp. 1440-1448 (2006).

SUMMARY OF THE INVENTION

In accordance with the present invention a method and a supporting system operating according to computer-executable instructions characterize tissue components of plaque within blood vessels. A BDC technique is used to generate a system transfer function for an imaging system. Homomorphic deconvolution (HDC) utilizes cepstral analysis of backscattered signals. The HDC technique replaces the aforementioned IWM BDC technique in a procedure for performing analysis of backscattered image signal data.

A method is described herein for acquiring ultrasound response data for vascular tissue. The method includes initially inserting at least a portion of a catheter into a vascular structure and activating a transducer portion of the catheter. Activation of the transducer portion results in an ultrasound signal being transmitted toward vascular tissue within a body. Thereafter, a scan line of backscattered ultrasound data is acquired from the vascular tissue. A system thereafter executes computer-executable instructions to apply a one-dimensional homomorphic deconvolution operation to digital data corresponding to the scan line of backscattered ultrasound data to render an estimated scan-line system transfer function while the catheter is inside the vascular structure. Ultrasound response data is calculated for the vascular tissue The system transfer function is thereafter calculated based upon a system transfer function that is based upon the estimated scan-line system transfer function.

In a particular embodiment, the system transfer function is generated from a set of separately calculated scan-line system transfer function estimates rendered from sets of scan-line ultrasound data obtained for a same image frame.

The invention is implemented in a system that is configured to carry out the aforementioned method steps as well as a physical computer-readable medium containing computer-executable instructions for facilitating carrying out the above-mentioned steps.

BRIEF DESCRIPTION OF THE DRAWINGS

While the claims set forth the features of the present invention with particularity, the invention, together with its objects and advantages, may be best understood from the following detailed description taken in conjunction with the accompanying drawing of which:

DETAILED DESCRIPTION OF THE DRAWINGS

Figure 4:
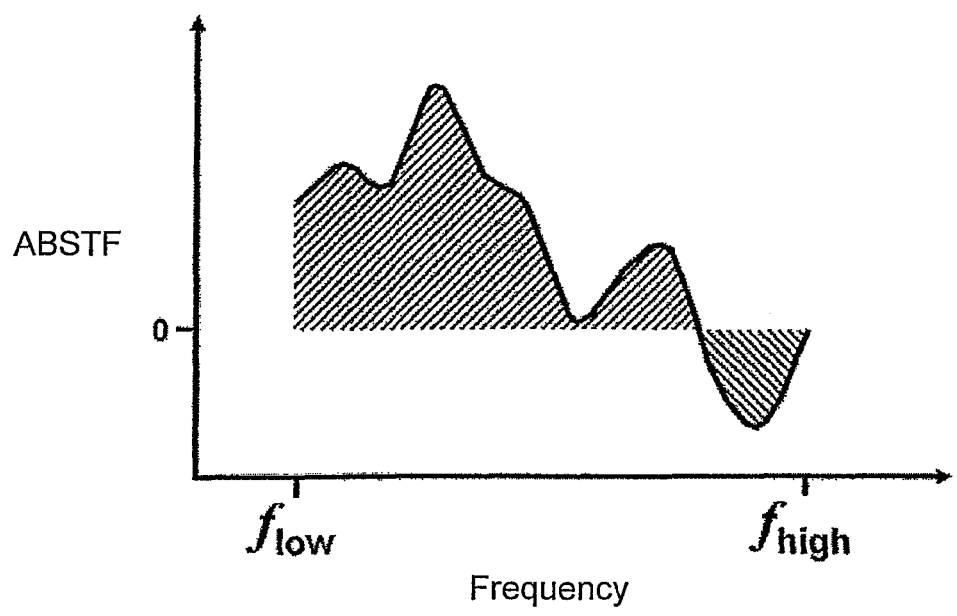
FIG. 4 is an exemplary graphical depiction of an apparent backscatter transfer function (ABSTF) for an echo signal segment.

Characterizing various types of tissue that make up plaque found within blood vessels facilitates classifying the larger plaque structures in order to diagnose and treat vascular disease. In the context of the disclosed system, a parameterized property of interest is a backscatter power coefficient that is indicative of how strongly a microscopic volume of tissue scatters ultrasound back to an ultrasound source. In accordance with exemplary embodiments system-dependent spectral characteristics of the IVUS system 100 are deconvolved from the backscatter power from tissue using a blind deconvolution operation, in particular homomorphic deconvolution (see FIG. 7 described herein below). Deconvolution is an engineering discipline that improves the fidelity in electronic signals by removing (i.e., deconvolving) features of the signal that depend only on the imaging or measurement system (e.g., IVUS system). Blind deconvolution is a process in which the system-dependent characteristics are not a priori known. Such a process is described, by way of example, in Jirik and Taxt, IEEE Ultrasonics, Ferroelectrics, and Frequency Control, Vol. 53, No. 8, 2006, pp. 1440-1448. The resulting normalized backscatter power is referred to as the apparent backscatter transfer function (ABSTF). FIG. 4 graphically depicts an example of an ABSTF (in logarithmic dB scale) derived from the backscatter power coefficient for an ultrasound echo signal segment. The ABSTF approximates the backscatter power coefficient. The ABSTF is depicted over a measured frequency band corresponding to, for example, the operating frequency spectrum of a system. The area under the ABSTF curve (representative of an echo signal segment's total backscatter power over a given frequency range) normalized (e.g., divided) by the bandwidth ($f_{high}-f_{low}$) to account for unequal and/or variable bandwidths, is referred to herein as the integrated backscatter (IB). The IB thus represents the average of the ABSTF curve over a specified bandwidth.

The polarity of the signal value is maintained during the IB calculation. Thus, the portions of the graph above the "0" amplitude level indicate a positive contribution to the IB value. The portions of the graph below the "0" amplitude level indicate a negative contribution to the IB for a backscatter signal. The IB provides a measure of the frequency-averaged backscatter power of a particular tissue volume over a designated frequency band from $f_{low}$ to $f_{high}$.

Figure 5:
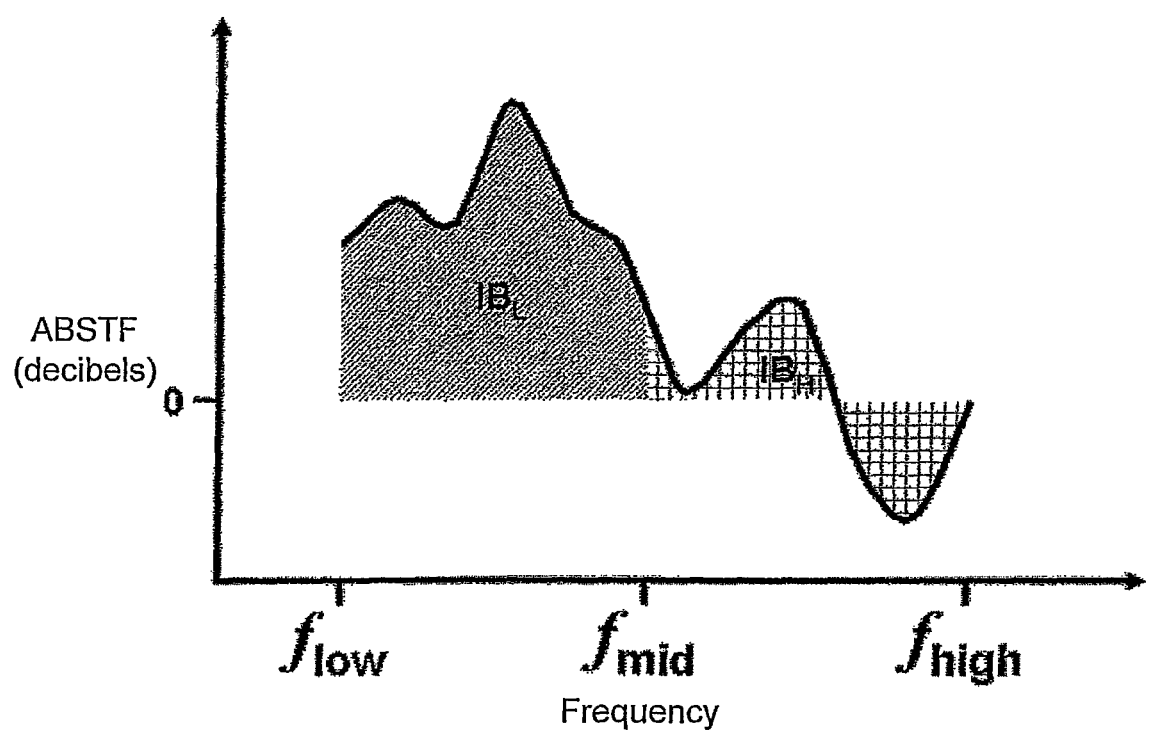
FIG. 5 is an exemplary graphical depiction of an ABSTF for an echo signal segment that has been split into low and high frequency bands for calculating low and high IB parameter values.

Turning to FIG. 5, the disclosed system and method for characterizing plaque tissue in blood vessels improve the spectral resolution of IB-based characterization schemes by splitting the operating frequency range of an IVUS system into at least two bands. In the exemplary embodiment the operating range ($f_{low}$ to $f_{high}$) is split into a low band ($f_{low}$ to $f_{mid}$) and a high band ($f_{mid}$ to $f_{high}$). Alternatively the operating frequency range is split into even more sub-bands. Furthermore, while the illustrative example designates two, non-overlapping, adjacent bands, alternative embodiments utilize overlapping bands as well as ones with gaps between one or more bands of interest.

Based upon the split frequency range, an $IB_{low}$ parameter value and an $IB_{high}$ parameter value are calculated from the ABSTF in the respective low and high sub-bands of the full operating band. Yet other examples of potentially useful IB-based parameters providing enhanced spectral resolution for characterizing plaque tissue (e.g., by applying to a tissue characterization decision tree) include: (1) a difference between the $IB_{low}$ and $IB_{high}$ values, and (2) a ratio of $IB_{low}$ to $IB_{high}$.

Furthermore, other embodiments of the present invention utilize the split spectrum of the ABSTF to render other spectrally resolved parameterized data. Examples include slope and intercept parameters from a linear regression of the ABSTF within each sub-band.

The spectrally resolved parametric data values from at least two distinct bands within a larger operating frequency range of an ultrasound system are thereafter applied to characterization criteria to render a characterization for the tissue corresponding to the intravascular ultrasound signal segment. Experimentation has confirmed that splitting a larger available frequency band into two or more sub-bands for purposes of rendering a set of IB parameters from a same intravascular ultrasound echo segment, facilitates identifying particular types of tissue (e.g., fibro-fatty and necrotic core) within plaque deposits in blood vessels.

It is furthermore noted that both analog and/or digital processing methods are potentially used to define the sub-bands in a split-spectrum analysis that renders parameter values representing the spectral power response of intravascular ultrasound echo signal segments in specified sub-bands (to render the IB parameter values for each spectral band). Furthermore, the various system implementations utilize a variety of components to analyze and render IB parameters, including: analog circuitry and digital circuitry as well as hardware/firmware/software and combinations thereof.

An exemplary IVUS (intravascular ultrasound) system includes an ultrasonic probe device mounted upon a flexible elongate member for insertion into vasculature. The system furthermore includes a computing device comprising memory for storing computer executable instructions associated with rendering a set of IB parameter values for a given ultrasound echo signal segment corresponding to particular sub-bands of a larger band associated with an ultrasound system. The computer executable instructions apply a blind (homomorphic) deconvolution technique to received, partially processed echo signals to obtain a system transfer function which is thereafter used to render an apparent backscatter transfer function IB parameter. Additional computer executable instructions stored on the computing device apply the set of IB parameter values to plaque tissue characterization criteria.

In the detailed description of the exemplary embodiment that follows, like element numerals are used to describe like elements illustrated in one or more figures.

Figure 1:
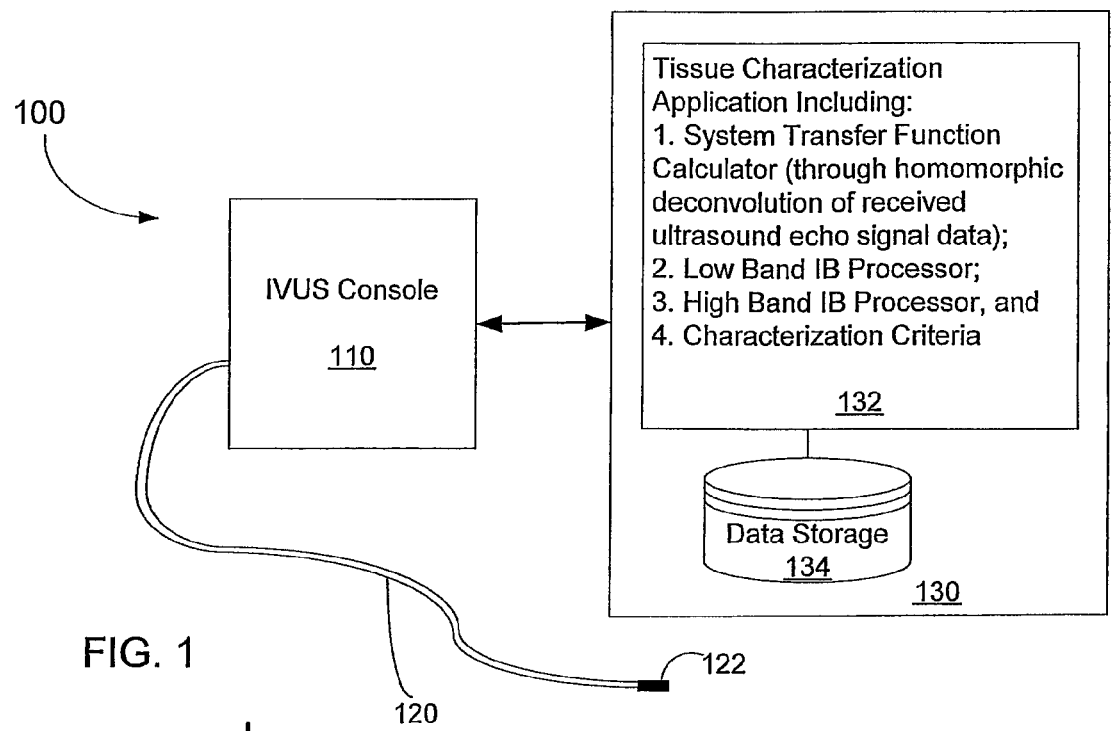
FIG. 1 illustrates a tissue-characterization system suitable for carrying out a tissue/plaque characterization scheme including an integrated backscatter parameter generator that generates, for each one of a set of transduced echo signal segments, a system transfer function and tissue signal extractor (based on calculated transfer function)

Turning to FIG. 1, a vascular plaque tissue characterization system 100 is schematically depicted. An intravascular ultrasound console 110 is communicatively coupled to an IVUS catheter 120. The IVUS catheter 120 comprises a distally mounted ultrasound transducer probe 122 that acquires backscatter data (e.g., IVUS data) from a blood vessel. In accordance with known IVUS catheters, the catheter 120 is maneuvered through a patient's body (e.g., via a femoral artery) to a point of interest. The transducer probe 122 is then controlled, via the console 110 to emit ultrasound pulses and thereafter receive echoes or backscattered signals reflected from vascular tissue/plaque and blood. Because different types and densities of tissue absorb and reflect (backscatter) the ultrasound pulse differently, the reflected ultrasound echo data (i.e., IVUS data) signals transmitted back to the console 110 by the IVUS catheter 120, are converted by characterization software into images of vascular objects. It should be appreciated that the IVUS console 110 depicted herein is not limited to any particular type of IVUS console, and includes all ultrasonic devices known to those skilled in the art (e.g., In-Vision Gold and s5™ systems of Volcano Corporation). It should further be appreciated that the IVUS catheter 120 depicted herein is not limited to any particular type of catheter, and includes all ultrasonic catheters known to those skilled in the art. Thus, for example, a catheter having a single transducer (e.g., adapted for rotation) or an array of transducers (e.g., circumferentially positioned around the catheter) is within the spirit and scope of the present invention.

Known imaging applications executed on an IVUS console (e.g., console 110) or a communicatively coupled computing device (e.g., computing device 130), render a variety of image types from received echo information. A first type of imaging application converts ultrasound echo signal data into gray scale images reflecting the relative strength of the echo signal returned by the objects within the transducer probe 120's field of view. In such imaging applications, the relatively light and dark regions indicate different tissue types and/or densities.

Other imaging applications, such as a tissue characterization application 132 that includes computer executable instructions executed on the computing device 130 communicatively coupled to console 110, renders tissue type information based upon the spectral (e.g., frequency and power) characteristics of the echo information received by the console 110 from the catheter 120. In accordance with an illustrative embodiment, the characterization application 132 includes computer executable instructions that, when processed by the computing device 130, render a system transfer function via a homomorphic deconvolution technique (see, FIG. 7 described herein below).

Thereafter, the system transfer function is applied to received ultrasound echo signal data to render an apparent backscatter transfer function. In the illustrative example, IB parameter values are rendered from spectral analysis of the ultrasound echo information. In particular, IB parameter values are rendered for each of multiple sub-bands of an operating frequency band of the system 100 by corresponding IB processors (e.g., Low Band IB Processor and High Band IB Processor). The Low and High Band IB processors are identified separately in FIG. 1. However, in an exemplary embodiment, a single dynamically configurable IB processor renders IB parameter values on the fly from one of multiple selectable frequency sub-bands.

Figure 2:
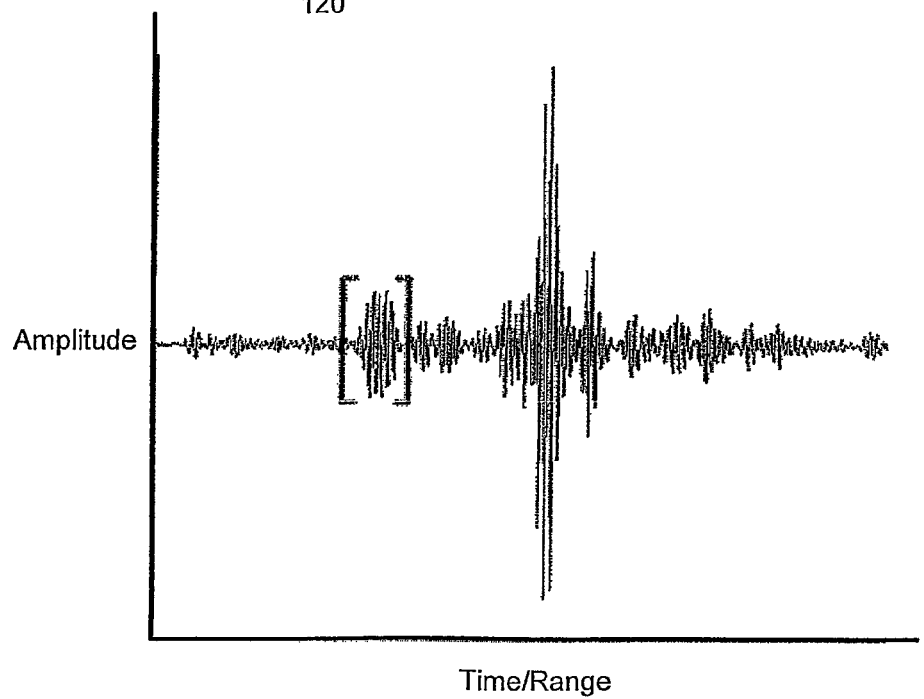
FIG. 2 illustrates an exemplary graphical depiction of a received ultrasound echo signal's amplitude over a period of time.
Figure 3:
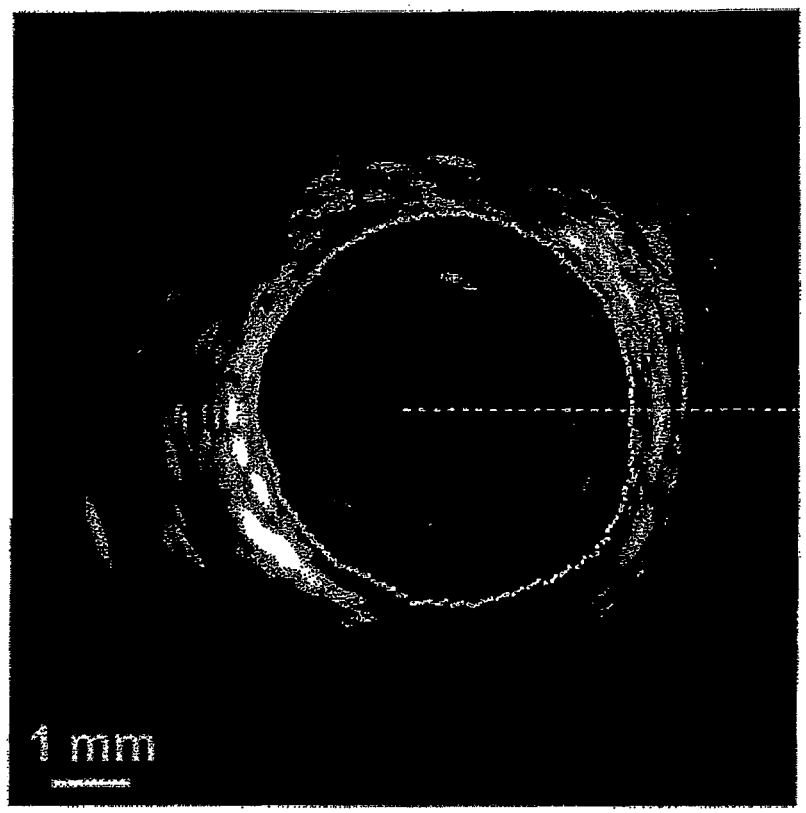
FIG. 3 is an exemplary grayscale ultrasound image of a vessel's cross-section.

Furthermore ultrasound power spectra from which IB parameter values are calculated in any of many potential ways. In illustrative examples, described further herein below, the ultrasound power spectrum (dividable into at least two sub-bands corresponding to Low and High Band IB parameters) is calculated by applying either Fourier or autoregressive modeling techniques to an ultrasound echo signal segment (see, e.g., FIG. 2). With reference to FIG. 2, in an exemplary embodiment a bracketed segment of a portion of an ultrasound echo signal is digitized and provided to both the Low Band IB Processor (associated with a relatively low sub-band of an operating frequency range of system 100) and the High Band IB Processor (associated with a relatively high sub-band of the operation frequency range of system 100) of the characterization application 132 to render corresponding Low and High Band IB parameter values for the echo signal segment. Turning briefly to FIG. 3 showing an exemplary gray-scale IVUS image, in an exemplary embodiment, the system 100 correlates a time of receipt of the bracketed echo signal segment with a range (distance from a transducer element) along a scan line (the dotted horizontal line) in a field of view of an ultrasound probe.

The spectral resolution-enhanced IB parameter value sets extracted from the echo information rendered by the catheter 120 for a same echo signal segment are evaluated and applied to tissue characterization criteria that incorporate the frequency response signatures associated with particular types of plaque tissue. The IB parameter values are potentially applied in association with other extracted parameters rendered by other signal processors, to the characterization criteria incorporated in the characterization application 132, to render a tissue characterization for a point within a field of view of the ultrasound probe corresponding to an echo signal segment from which the IB parameter values were derived.

It is noted that while a tissue characterization is based on a single echo signal segment in the illustrative example described above, in alternative embodiments multiple echo signal segments and/or IB parameter values are combined with temporal/spatial neighbors to render values that exhibit improved signal/noise ratios. Thus, multiple echo signal segments from adjacent scan lines or repeated firings on a same scan line can be combined and presented to the Low and High Band IB processors. Also, multiple IB parameter values corresponding to the signal segments are potentially combined. In either case, the combination potentially improves the overall signal/noise ratio.

A data storage 134 stores the tissue characterizations rendered by the characterization application 132 based upon parametric information generated from the Low and High Band IB processors (and potentially other extracted parametric data) to the characterization criteria. The data storage 134 is, by way of example, any of a variety of data storage devices, including RAM, cache memory, flash memory, magnetic disks, optical disks, removable disks, SCSI disks, IDE hard drives, tape drives, optically encoded information discs (e.g., DVD) and all other types of data storage devices (and combinations thereof, such as RAID devices) generally known to those skilled in the art.

In the illustrative example, the tissue characterization application 132 exists as a set of one or more applications including computer executable instructions that make up the system transfer function calculator (using homomorphic deconvolution) and multiple integrated backscatter parameter value processor components corresponding to multiple frequency sub-bands for which IB parameter values are calculated for each ultrasound echo segment. In exemplary embodiments, the characterization application 132 comprises multiple applications/components executed on one or more computing devices (including multiple processor systems as well as groups of networked computers). Thus, the number and location of the components depicted in FIG. 1 are not intended to limit the present invention, and are merely provided to illustrate, by way of example, the environment in which an exemplary system operates. Thus, for example, a computing device having a plurality of data storage devices and/or a remotely located characterization application (either in part or in whole) is within the spirit and scope of the present invention.

Figure 6A:
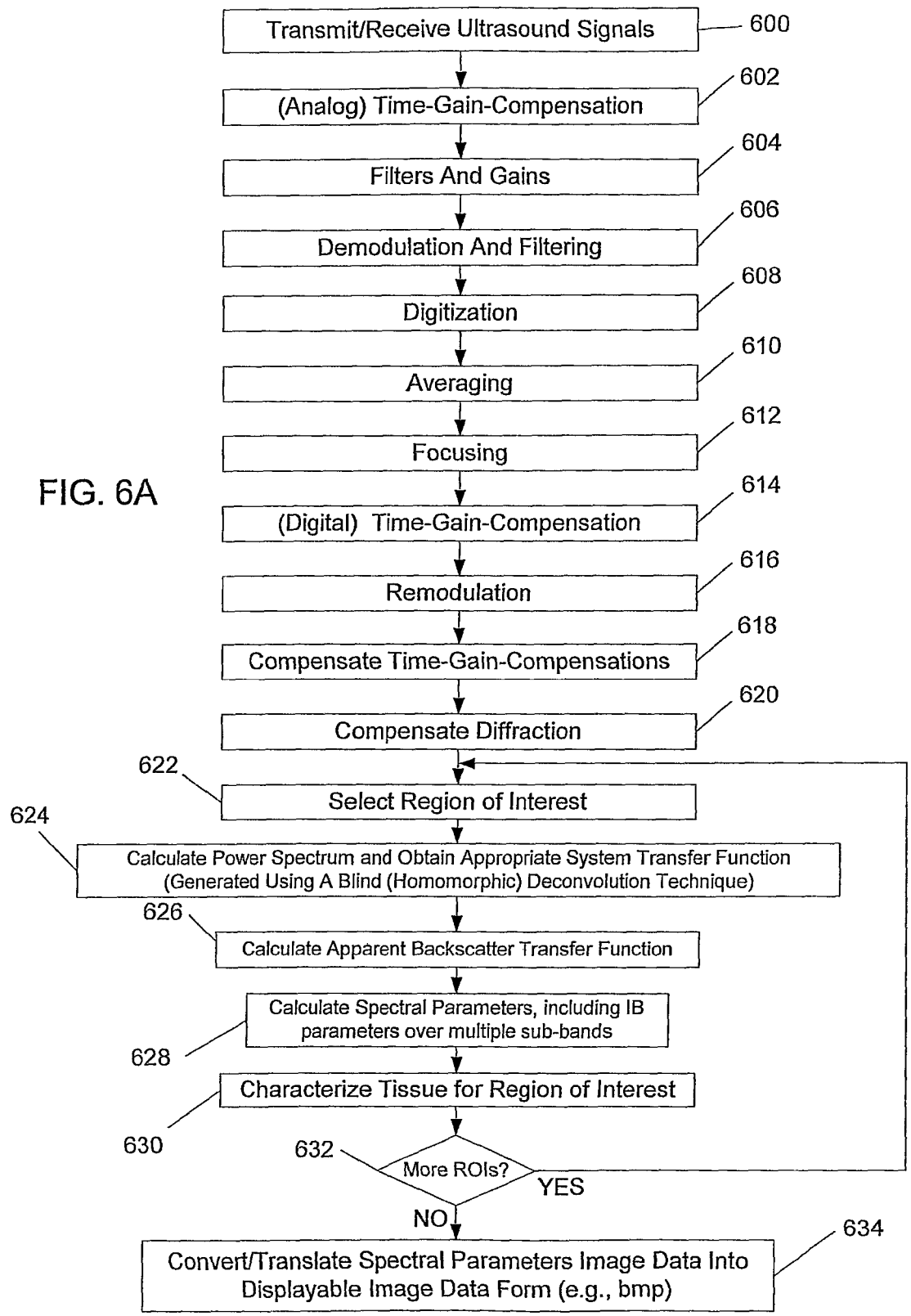
FIGS. 6a and 6b each describes a set of processing stages for rendering parametric information for characterizing plaque tissue.
Figure 6B:
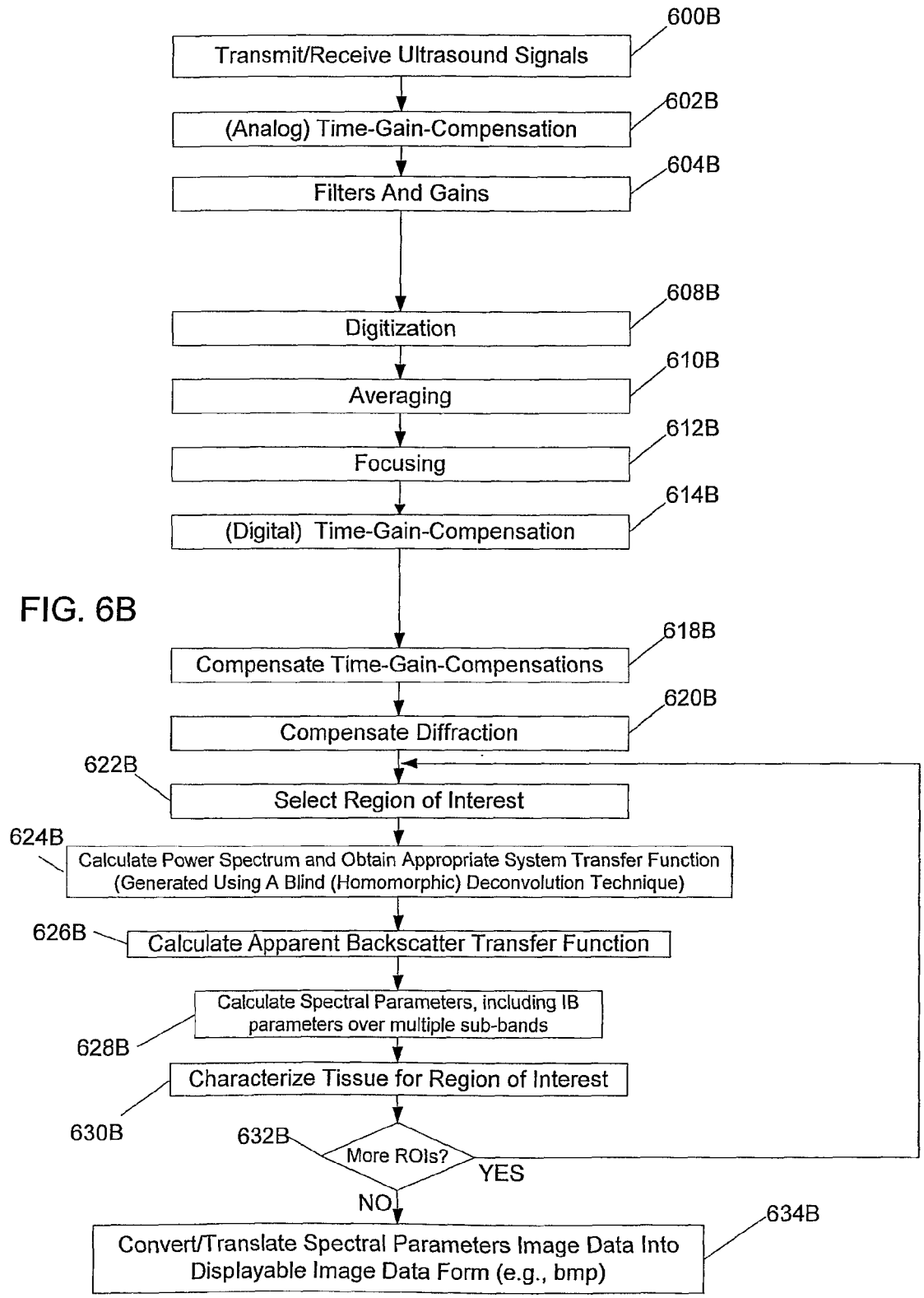

FIGS. 6a and 6b each describes an exemplary set of processing stages for rendering parametric information for characterizing plaque tissue in accordance with different raw IVUS signal processing architectures. Referring to FIG. 6a, a set of steps are summarized for processing data that is initially provided in the data domain (i.e., as baseband data)—requiring significantly less signal data to be stored since the digitized raw RF signal is converted to data components rather than preserving a digitized version of the time domain RF signal. In the exemplary embodiment, wherein the split-spectrum analysis is performed in the RF domain, "remodulation" of the data signal (back to the RF domain) is performed in preparation for generation of the ABSTF for the selected ultrasound echo signal segments.

During step 600 an ultrasound probe transmits ultrasound pulses and receives ultrasound echo signals from scatterers within the field of view defined by a set of scan lines. The received analog echo signals are passed to a patient interface module wherein, during step 602, the analog signals are time-gain compensated via amplifier circuitry to accommodate the inherent drop off of reflected energy as a function of distance from the ultrasound probe. Next, during step 604 the compensated analog signal is filtered and amplified in preparation for extracting a data signal.

Thereafter, during step 606 baseband data is extracted from the compensated analog echo signal by a demodulation and filtering stage. The resulting analog data signal is thereafter digitized during step 608. In an exemplary embodiment a 16 bit signed digital value is stored for each sample. However, in alternative embodiments more or fewer (e.g., 12) bits are used to specify each value.

In an exemplary embodiment, an averaging operation is performed on the digitized data during step 610 to improve a signal to noise ratio of the digitized data. Next, during step 612 a focusing operation is performed to render additional echo image data. Focusing (i.e., beamforming) combines signals from a neighborhood of array elements in order to improve sensitivity. A similar process can be performed with consecutive transmissions when using an ultrasonic probe that is comprised of a single element. Thus, while a signal segment is referred to herein in singular form, the ultrasound echo signal segment referred to herein is potentially a sum of multiple spatial or temporal echo signals received by the IVUS system. It is furthermore noted that for a given region of interest, multiple ABSTF functions/curves associated with points on a scan line and neighboring scan lines are combined to render an ABSTF for a given region of interest.

During step 614 additional time-gain compensation is applied to the focused digitized data signal. Thereafter, during step 616, the data signal is remodulated. Remodulation transforms data-domain data back to RF-domain data which is utilized by the Low and High Band IB processors.

During step 618 additional compensation operations are performed on the time-gain compensated time-domain signal.

During step 620 additional operations are performed on the modulated data to compensate for diffraction effects on the ultrasound echo signal.

Thereafter an echo signal segment corresponding to a region of interest in the ultrasound probe's field of view is selected in step 622. Selection of an echo signal segment, in an exemplary embodiment, comprises selecting an echo signal segment for multiple scan lines and points within a scan line to improve signal/noise characteristics. In an exemplary embodiment, the segments are independently processed through ABSTF and IB parameter calculations. The IB parameter calculations for each echo signal segment are averaged prior to application of characterization criteria during step 630 described herein below.

During step 624, the power spectrum of the region of interest of the compensated time-domain remodulated signal is calculated. A system transfer function is separately calculated using a blind (homomorphic) deconvolution technique. More specifically, in an exemplary embodiment, an average system transfer function is calculated for a full image frame (based upon system transfer functions calculated for a set of scan lines that make up the image frame) in accordance with the homomorphic deconvolution operation described herein below with reference to FIG. 7. Thus, for a single image frame containing multiple regions of interest, a single (average) system transfer function is calculated for the entire image frame and then obtained/accessed when processing the echo signal data for each one of multiple regions of interest in the image frame.

The ABSTF curve (See FIG. 4) is then calculated at step 626 based upon the information obtained during step 624. The ABSTF is the deconvolution of the system transfer function from the power spectrum of the region of interest. In an exemplary embodiment, the ABSTF is calculated as the log-spectral subtraction of the system transfer function from the power spectrum of the region of interest. In other embodiments the ABSTF can be calculated as the ratio of the power spectrum (in linear units as opposed to decibels) of the region of interest to the system transfer function (in linear units as opposed to decibels).

Based upon the selection of the region of interest during step 622, during step 628 spectrally distinct parameter values (e.g., IB values) are calculated for each of at least two sub-bands of a device's operation frequency band in accordance with the above-described IB parameter generation operation. Thereafter, the spectrally resolved IB parameter values for each echo signal segment for potentially multiple echo signal segments processed for a region of interest are submitted to tissue characterization criteria for classifying the tissue during step 630.

During step 630, the spectrally resolved IB parameters are applied in a variety of ways to tissue characterization criteria. In an exemplary embodiment, the Low Band IB parameter value corresponds to the IB parameter value from the low end of the system bandwidth (e.g., −20 dB level) to the mid-band, the High Band IB parameter value corresponds to the IB parameter value from the mid-band to the high end of the system bandwidth, and at least one IB parameter value comparison provided to the characterization criteria includes a difference between the High Band IB parameter value and the Low Band IB parameter value. The difference is a signed value representing the relative magnitudes of the High and Low IB parameter values. In yet another embodiment, the at least one IB parameter value comparison provided to the characterization criteria includes a ratio based upon the High Band IB parameter value and the Low Band IB parameter value.

As noted above, the IB parameter values for multiple echo signal segments associated with a region of interest are averaged spatially and/or temporally during step 626 or 628 to improve signal/noise characteristics. The spectrally resolved IB parameter values for each of the multiple echo signal segments are combined (e.g., averaged) prior to applying the averaged spectrally resolved signals to the characterizing criteria during step 630 to characterize the tissue in the current region of interest.

Next, at step 632 if additional regions of interest are available, then control returns to step 622. Otherwise, control passes to step 634 wherein the system applies previously determined characterizations for regions of interest to render displayable image data.

Briefly referring to FIG. 6B, the steps (with a B appended to reference numbers previously described with reference to FIG. 6A) in a time domain-based system are similar to the correspondingly identified steps in FIG. 6A. However, the time domain system that operates upon the analog signal does not perform the Demodulation and Filtering step 606 and the Remodulation step 616 that are needed in the baseband-based system represented in FIG. 6A.

Figure 7:
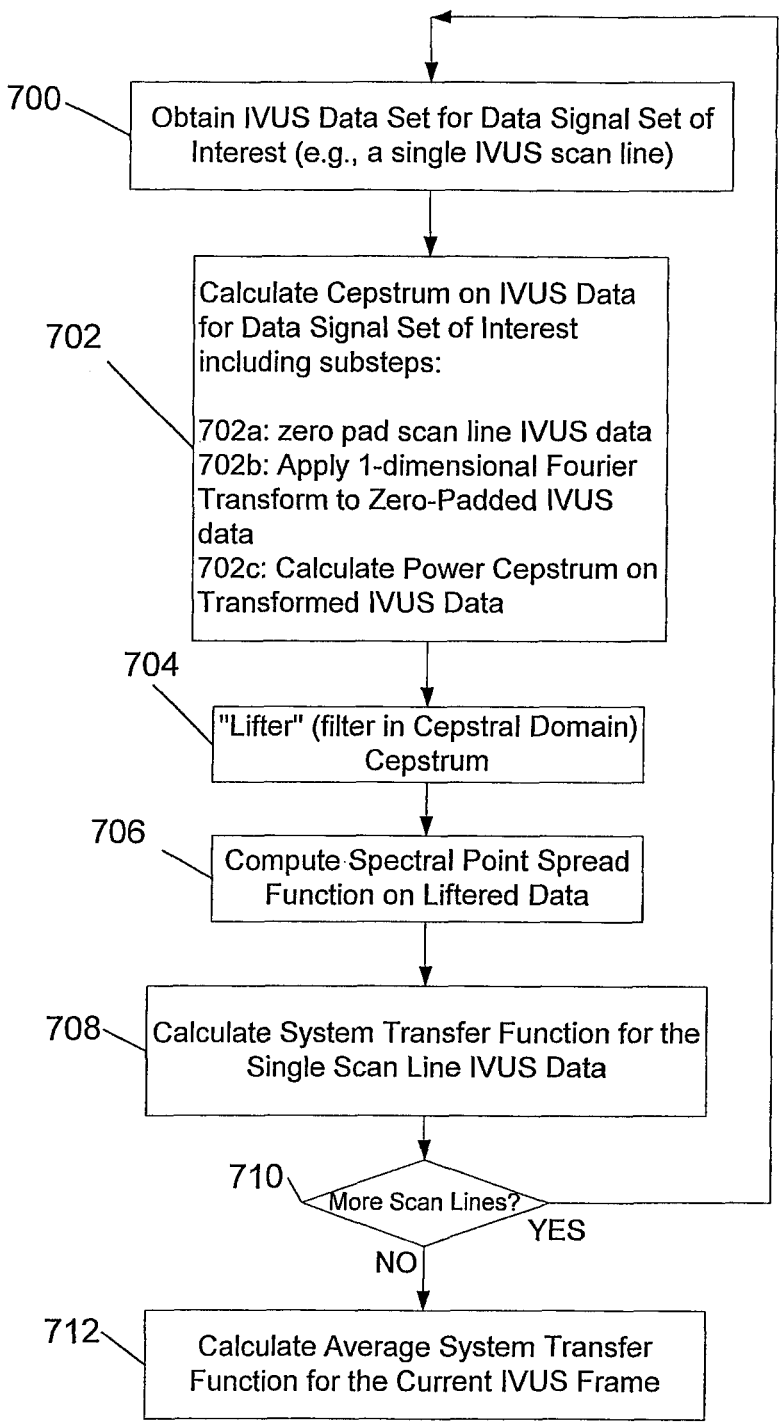
FIG. 7 is a flowchart summarizing an exemplary set of steps for generating a system transfer function using a HDC technique to render an estimate of the system transfer function based upon certain assumptions (i.e., system contributions to the recorded echo signal are present primarily in the low cepstral domain ranges)

FIG. 7 is a flowchart summarizing an exemplary set of steps for generating the system transfer function during step 626 (in FIG. 6a) and during step 626B (in FIG. 6b). The particular HDC algorithm for an exemplary system is provided herein below. At the time the summarized steps are performed, intravascular image data is available (e.g., a frame of data corresponding to 256 azimuth scan lines by 1024 samples (RF) per scan line. Such data is potentially acquired using a baseband system (corresponding to the steps summarized with reference to FIG. 6A), or an RF system (corresponding to the steps summarized with reference to FIG. 6B). Furthermore, in an exemplary embodiment, a transfer function is calculated for each one of 256 scan lines used to generate a single image frame, and thereafter the 256 individually calculated transfer functions are averaged to render a transfer function for the single image frame. The resulting image frame (average) transfer function is applied to the 256 scan lines making up the current image frame to render the echo signal for each of the 256 scan lines for the IVUS image frame. In the illustrative example, a single VH frame is calculated each heart cycle. Thus, the rate of calculating a new transfer function is on the order of once per second.

The above-described scan line "averaging" across a single frame approach is exemplary. A variety of ways for applying the resulting transfer function are contemplated in accordance with various exemplary embodiments. Alternatives include averaging across multiple frames, applying a time-based filter across multiple frames, averaging across multiple frames at a same scan line position, etc. In yet other embodiments, the transfer function calculated for a given scan line of image data is applied only to that single scan line.

A system transfer function calculated from the steps summarized in FIG. 7 is used to carry out tissue characterization and VH IVUS image generation according to the previously summarized methods. In summary, this method comprises acquiring a set of IVUS data (step 700), calculating the power cepstrum of the acquired IVUS data (step 702), liftering (i.e., filtering in the cepstral domain) the cepstrum (step 704), and a system transfer function is calculated from the filtered cepstrum (step 706). While the power cepstrum is utilized in the illustrative embodiment, alternative embodiments are contemplated that use, for example, a complex cepstrum. The steps of FIG. 7 are described in detail herein below.

The series of mathematical operations performed on the IVUS data acquired during step 700 represent a 1 dimensional (along a scan line) HDC approach that provides a 1 dimensional system transfer function for the IVUS data acquisition system. The 1D HDC can be performed on an entire scan line (1024 data points) or on a portion of the scan line.

During step 700, an IVUS data set is obtained for a data signal set of interest. By way of example the data signal set of interest is a scan line (beam) directed outwardly from an IVUS probe into a blood vessel. However, other regions of interest will be used in alternative embodiments. The data set for a single beam is, by way of example, one of a set of 256 beams that make up a single IVUS data frame from which the system generates a single IVUS (cross-sectional) image frame. Thus, the IVUS data set comprises a set of data points along a particular beam extending outwardly from the IVUS probe. Step 700 generally entails the steps leading up to and including step 622 in FIG. 6A. The data signal set of interest in FIG. 6A corresponds to a single scan line. The manner of acquiring and processing raw IVUS data to render the IVUS data signal set of interest varies according to various embodiments. In an exemplary embodiment, a set of 1024 filtered and compensated data points (samples), representing an ultrasound echo signal for a single IVUS scan line, are provided for a beam direction constituting a selected region corresponding to the data signal set of interest. Furthermore, each image frame consists of a set of 256 scan lines (data signal sets of interest from which system transfer functions are determined according to the steps described herein below). The time period between samples in an exemplary embodiment is 10 ns. This sampling period corresponds to a Nyquist frequency of 50 MHz (i.e., 50 MHz=0.5*(1/10 ns)) that represents the highest frequency which can be measured in a digitally sampled analog signal without aliasing. Shorter sampling periods (e.g., 2.5 ns or 5 ns) are necessary when using higher IVUS frequencies. Those skilled in the art will readily appreciate that increasing the sampling rate generally improves the precision of the system. A drawback of increasing sampling rate is increased processing load and memory consumption due to increased data volume. Other considerations include the availability of commercially available analog-to-digital converters from which raw echo signal samples are rendered, available memory, processor speed, etc. For example, state of the art signal sampling hardware for IVUS is presently about 400 MHz. However, the maximum sampling rate will increase as technology progresses.

The steps that follow are performed to render a system transfer function for the acquisition and processing of IVUS image data in a single beam direction (region corresponding to the data signal set of interest) in accordance with an illustrative embodiment. A set of 256 transfer functions are calculated (in 256 distinct directions) for each VH IVUS frame, and thereafter the 256 transfer functions are averaged to render an averaged transfer function for the VH IVUS frame. Thus, for a VH system wherein a VH frame is calculated for each heart cycle, a new averaged transfer function is rendered on the order of once every second.

Figure 8:
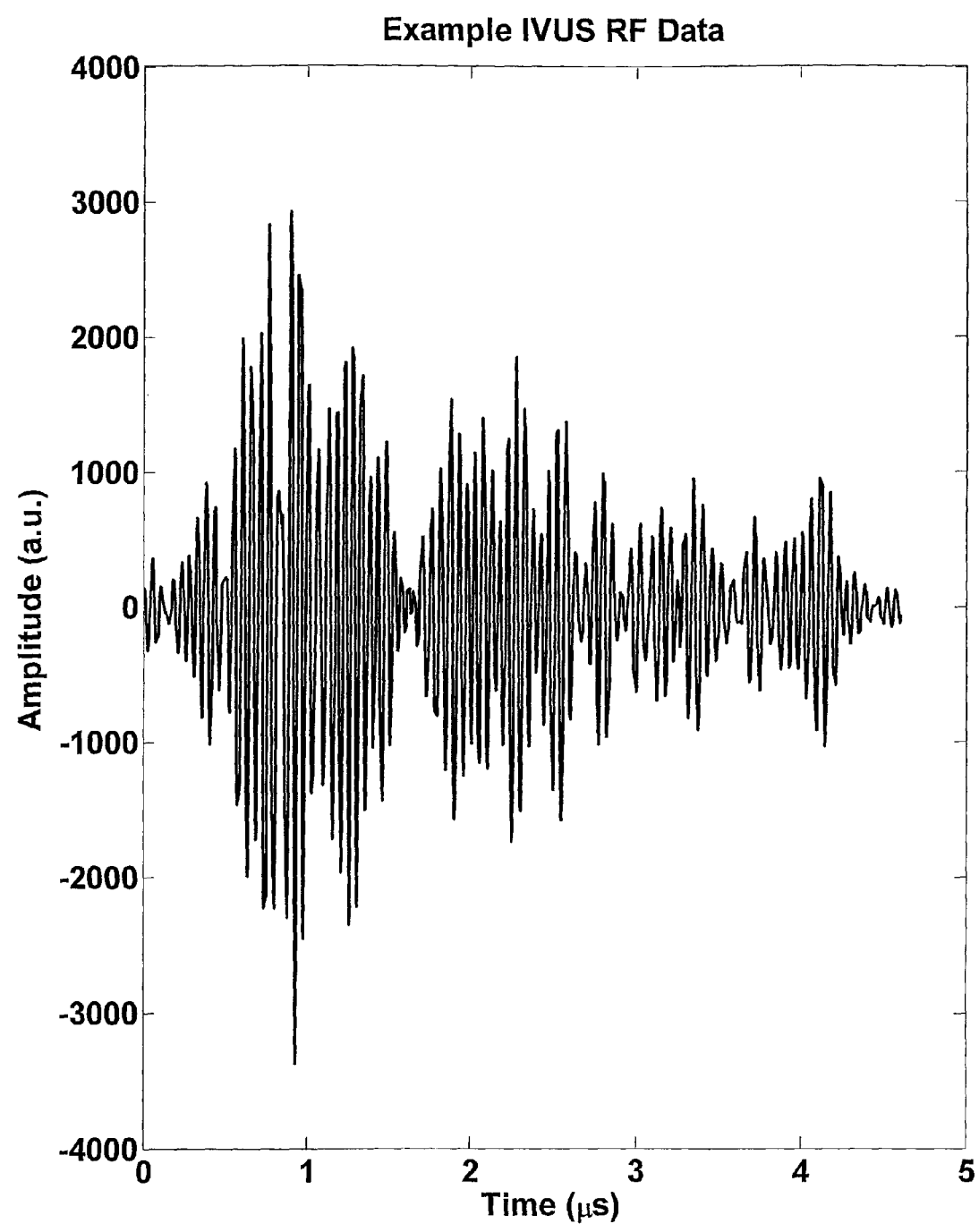
FIG. 8 depicts an exemplary IVUS echo signal representation.

During step 702 a cepstrum is calculated from the IVUS data set provided during step 700. A graphical example of a data set for a transduced IVUS echo signal for a single beam is depicted in FIG. 8. Initially, during step 702a, the IVUS data set (1024 points) for the scan line of interest is zero padded along the scan line by adding 3072 zero-value points to the distal "end" of the scan line (in relation to the IVUS probe). In an exemplary embodiment the zero padding extends the beam to about 30 mm. Thus for a given scan line a total of 4096 data points are present in the IVUS data set used to calculate the cepstrum. The zero-padded data set is referred to herein as "$g_m(n)$", where n corresponds to the sample number (0 to 4095) and m corresponds to the scan line (beam) number (0-255).

Zero padding the original IVUS data set in the time domain provides the effect of interpolating the signal in the frequency domain. Experimentation has shown that zero padding improves the output of the homomorphic deconvolution signal processing operation described herein in the context of a VH application. The choice of the length of the zero padding time-series data sequence involves weighing desired accuracy and computational performance. The present example uses zero padding to render a data point set for further signal processing that is four (4) times the length of the actual IVUS data set. Zero padding to increase the size of the data set by a power of two (i.e., 2, 4, 8, etc.) is convenient for application of a Fast Fourier Transform to the resulting data, but is not a requirement. Four is the preferred factor by which the length is increased by the zero padding. Empirically, increasing the factor beyond four does not significantly improve accuracy but does increase computational load.

After zero padding the IVUS data set during step 702a, during step 702b a one-dimensional Fourier transform is applied to the zero padded IVUS data set for a single beam to render "Fourier data" $G_m(f)$ corresponding to the frequency spectrum of the zero padded IVUS data set. An exemplary (power) frequency spectrum for the Fourier data is provided. The Fourier data is thus represented by the following equation:

$$G_m(f)=F\{g_m(n)\} \quad (1)$$

Figure 9:
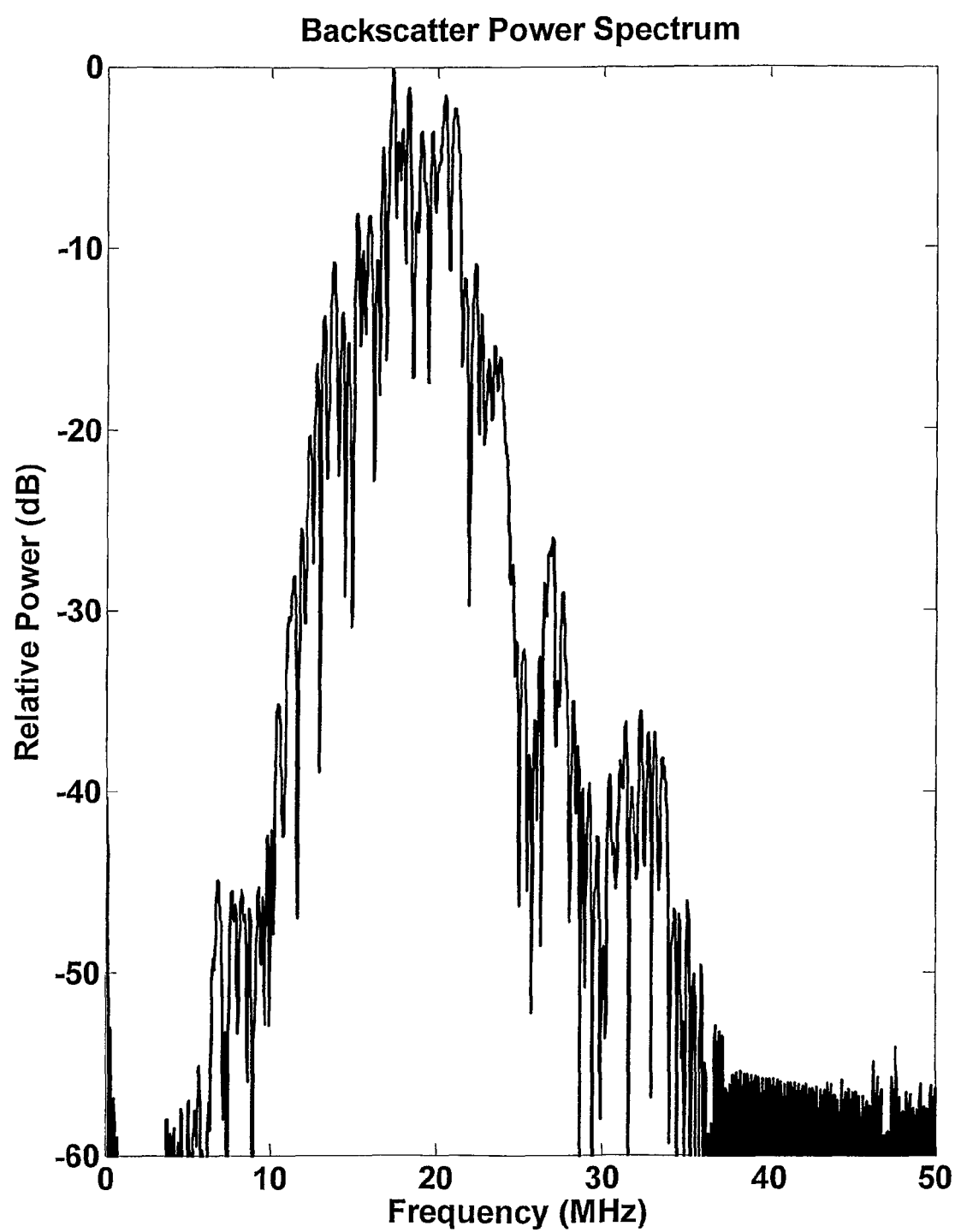
FIG. 9 depicts an exemplary backscatter power spectrum derived from the IVUS echo signal depicted in FIG. 8.

Turning briefly to FIG. 9, a plot representing 20*log 10(|Gm(f)|), or the power spectrum is provided.

Thereafter, during step 702c a "power cepstrum" is calculated (see, equation 2 below) by taking the inverse Fourier transform of the absolute value of the natural logarithm of $G_m(f)$.

$$\hat{g}_m(n)=F^{-1}\{\ln(|G_m(f)|+\text{bias})\} \quad (2)$$

Figure 10:
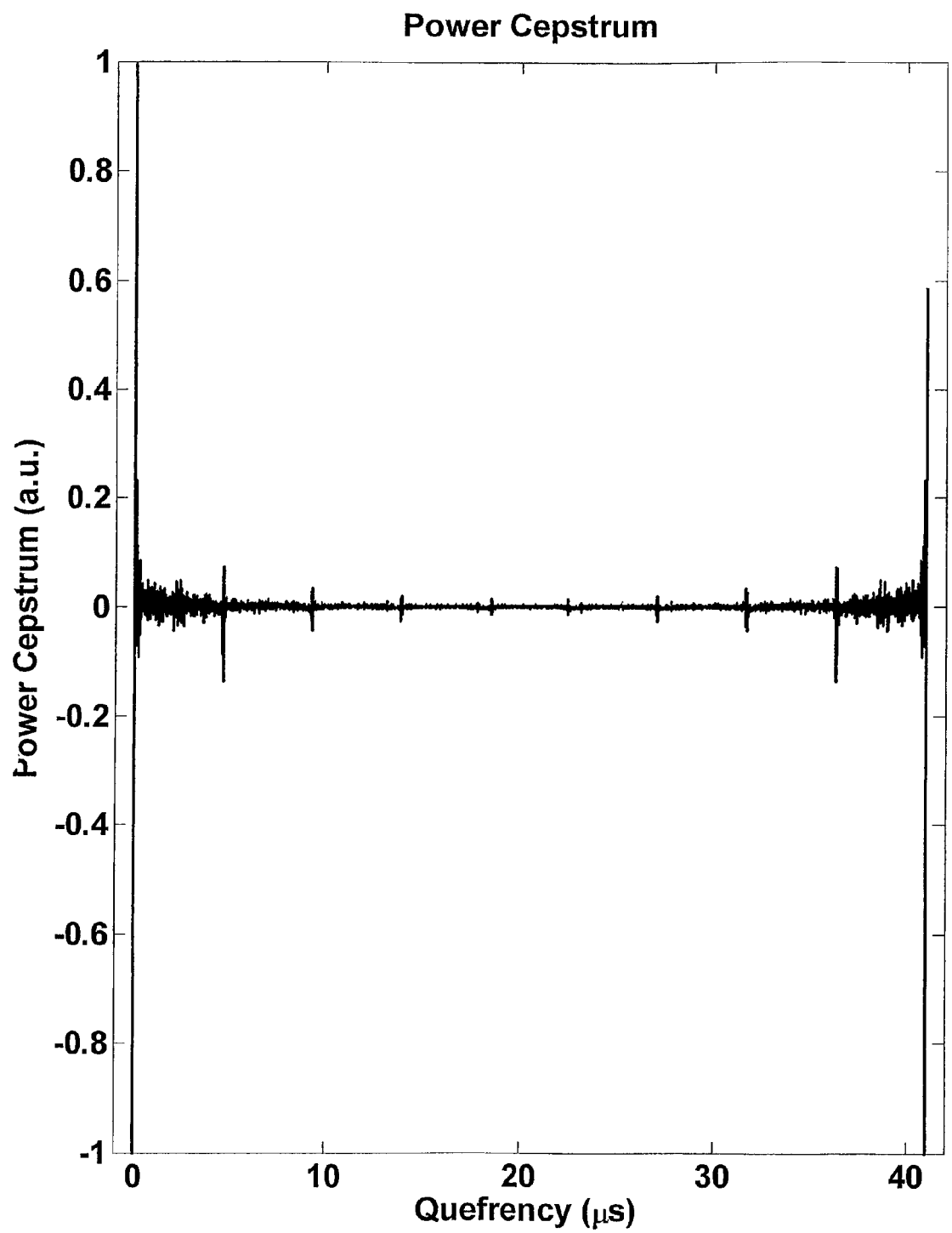
FIG. 10 depicts an exemplary power cepstrum derived from the power spectrum depicted in FIG. 9.

With regard to the above equation, a small bias value is added to ensure that a non-zero value is provided when taking the natural logarithm of $G_m(f)$. A suitable value for the bias parameter is 0.01 Nepers (or Np). In the illustrative example, the value of individual $G_m(f)$ is generally in the range of zero to about 100,000 in a system with 16-bit processing. In such circumstances that value for the bias value can be up to 0.1. The bias value should not be much less than 0.01 as that can result in a potentially large negative natural log value for values of $|G_m(f)|$ that are very near zero. By taking the absolute value of the Fourier data $G_m(f)$ before performing the inverse Fourier transform the power cepstrum is rendered. Turning briefly to FIG. 10, an exemplary power cepstrum rendered by equation (2) is provided.

Figure 11:
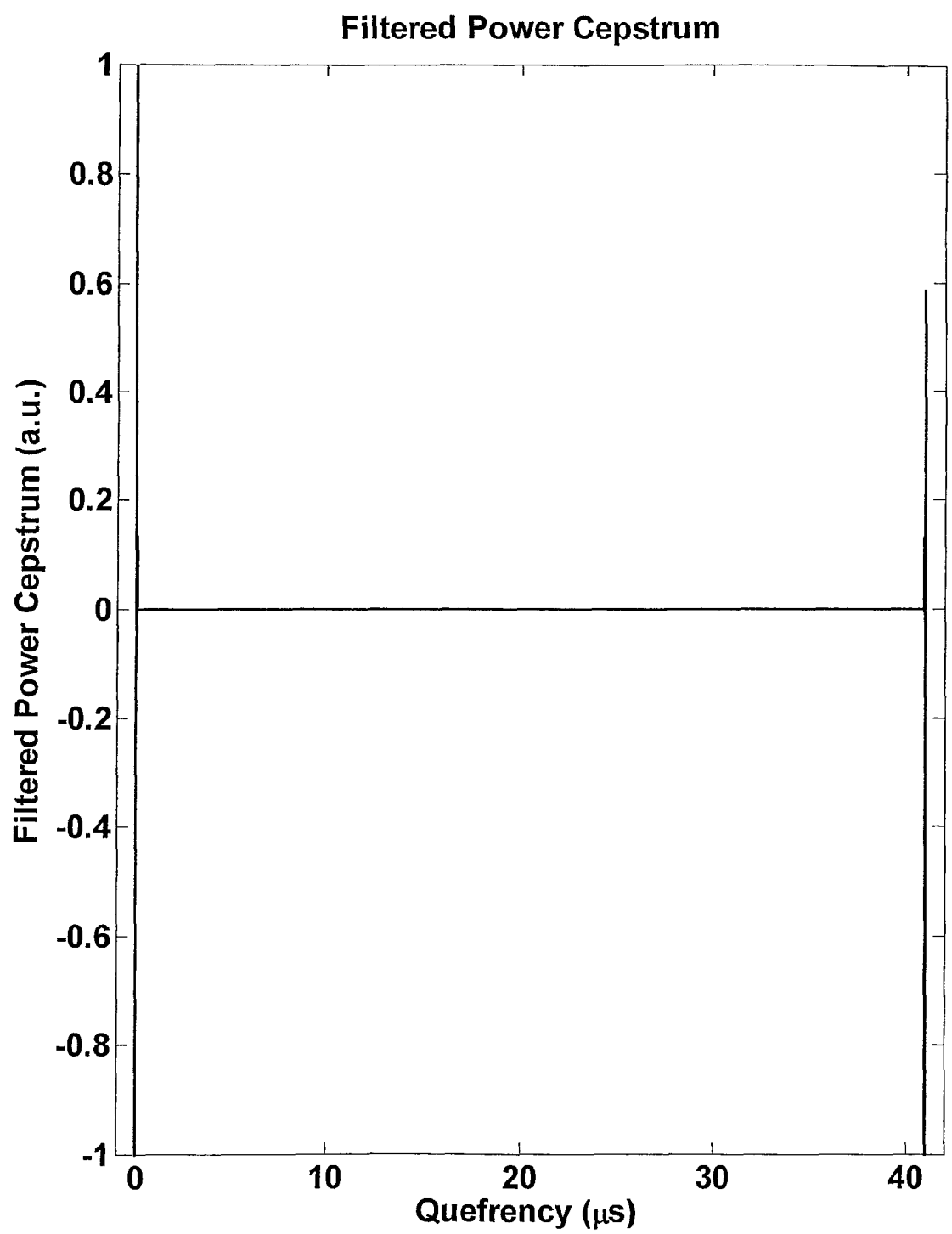
FIG. 11 depicts a (low pass) filtered power spectrum rendered by the system to remove tissue effects from the received signal.

Thereafter, during step 704 the power cepstrum is liftered (i.e., filtered in the cepstral domain) using a low pass filter in order to extract a "cepstral point spread function" (see, FIG. 11) from the power cepstrum rendered during step 702. The filtering step 704 is intended to remove the tissue effects from the signal and leave the (low cepstral domain (quefrency) values) system effects. The pass band of the low pass filter is, by way of example, 0.0 to 0.003 normalized quefrency (cepstral domain) units (or 0 to approximately 122.88 ns) for a system having a sample rate of 100 MHz. The filtering operation is summarized by the following equation (3):

$$\hat{h}_m(n)=b(n)\cdot\hat{g}_m(n) \quad (3)$$

In the exemplary embodiment, the filtering function b(n) is carried out by a fifth order Butterworth filter with a sample locus parameter of 0.003. Higher order filters are also suitable for VH IVUS. Also, a locus range of 0.003 to 0.005 is also suitable for VH IVUS. Loci greater than 0.005 do not adequately remove tissue effects, and loci less than 0.003 render an estimate for the system transfer function that has a substantially greater bandwidth than one would expect—leading to a present belief that the estimate is inaccurate.

Furthermore, while a Butterworth filter is used in the exemplary embodiment, other low-pass filters are contemplated in alternative embodiments. Other classes of potentially suitable low-pass filter classes include: Chebyshev, Bessel, Elliptic and Legendre. The choice of a Butterworth filter for the present embodiment is that the filter has a relatively flat response curve in the selected pass band. The other filter classes exhibit greater variance within the pass band which leads to less desirable, though still potentially acceptable, results. A Chebyshev filter typically exhibits a steeper roll-off than a Butterworth filter, but this characteristic does not appear to affect the VH IVUS applications. In addition the Chebyshev filter potentially exhibits a ripple in the pass band which can be undesirable. A Bessel filter exhibits a non-flat response curve in the desired pass band which is not desirable. An Elliptic (Cauer) filter can exhibit undesirable ripple in the pass band and stop band. A Legendre (Optimum "L") filter is a compromise between Butterworth and Chebyshev filters. A Legendre filter is similar to a Butterworth filter in that there is no ripple in the passband, but it does not have as flat a response. It is similar to a Chebyshev filter in that it has a steep roll-off.

Furthermore, in yet other alternative embodiments, high-pass filters are employed to remove the system components on every received data signal—leaving the purported image signal. In such cases, there is no opportunity to determine an average transfer function since it is removed from the transformed signal at this stage.

Thereafter, during step 706 a system transfer function $H_m(f)$, also referred to as the amplitude spectrum, is calculated by taking the exponential of the Fourier transform of the cepstral point spread function. The "exponential" operation reverses the previously applied natural log operation. The operation of step 706 is summarized by the following equation (4):

$$H_m(f) = \exp(F\{\hat{h}_m(n)\}) \quad (4)$$

Figure 12:
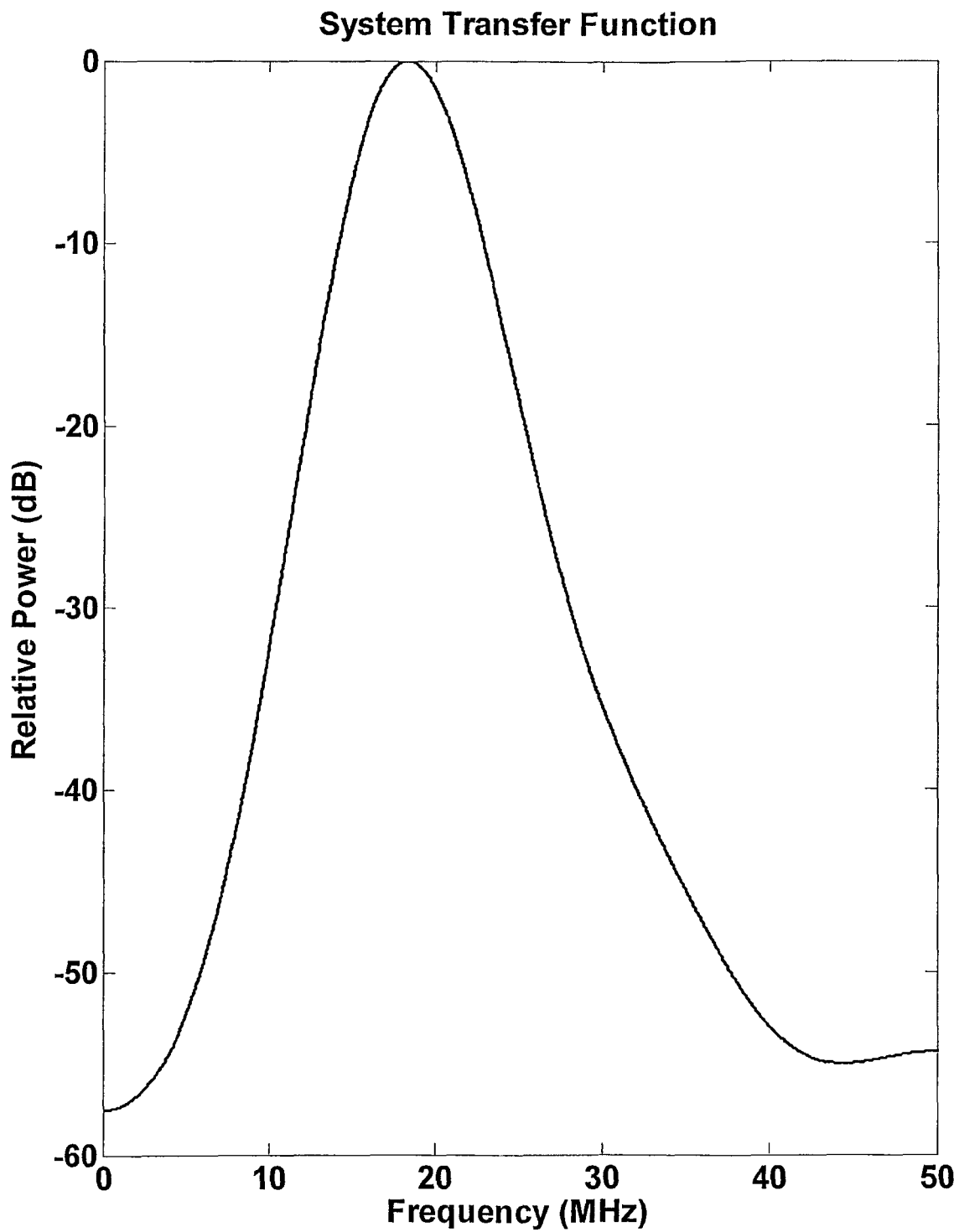
FIG. 12 depicts a system transfer function rendered for a single scan line (beam) in an IVUS image frame containing, for example, 256 scan lines/beams.

During step 708 a system power transfer function $P_m(f)$ is rendered for a single scan line (m) in the form of a "power spectrum" of the previously calculated system transfer function $H_m(f)$. See, FIG. 12. In particular a square of the absolute system transfer function is calculated over the set of points along a currently selected scan line (m). The operation of step 708 is summarized by the following equation (5):

$$P_m(f) = |H_m(f)|^2 \quad (5)$$

The above-described steps are repeated (m) times to render a system power transfer function $P_m(f)$ for each scan line in a frame. Thus, at step 710 if additional scan lines need to be processed then control returns to step 700 wherein a next scan line (data signal set of interest) is processed. After each scan line has been processed control passes from step 710 to step 712.

During step 712 an overall average system power transfer function for an IVUS frame P(f) is calculated as the average system power transfer function across the set of (m) scan lines according to equation (6):

$$P(f) = \frac{1}{M} \sum_m P_m(f) \quad (6)$$

It is noted that the scope of the input to the averaged system power transfer function differs in accordance with various embodiments. For example, in an alternative embodiment, the set of transfer functions for individual scan lines are maintained/applied on an individual scan line basis. In other embodiments only a fraction of the scan lines (e.g., every second, third, fourth, etc. scan line) is processed and thereafter averaged during step 712 to render an overall average system transfer function. In yet other embodiments, the averaging operation is carried over to multiple frames.

Upon completion of step 712, the average system power transfer function is available for application to received signals during spectral analysis and tissue characterization operations discussed herein below with reference to FIG. 13.

How often the system transfer function is re-calculated differs according to various embodiments. In the exemplary embodiment, a system transfer function is calculated and used for each processed IVUS image frame. In other embodiments a single system power transfer function rendered during step 712 is applied over multiple IVUS image frames.

In the illustrative example, the transfer function is recalculated for each frame. Such continuous calculation enables compensating for variations in performance of transducer elements over the course of an imaging procedure and facilitates averaging across multiple frames (not just across scan lines). Thus, the effect of a single noisy frame can be minimized. However, the frequency with which the transfer function is calculated and/or otherwise updated will vary in accordance with various embodiments.

Figure 13:
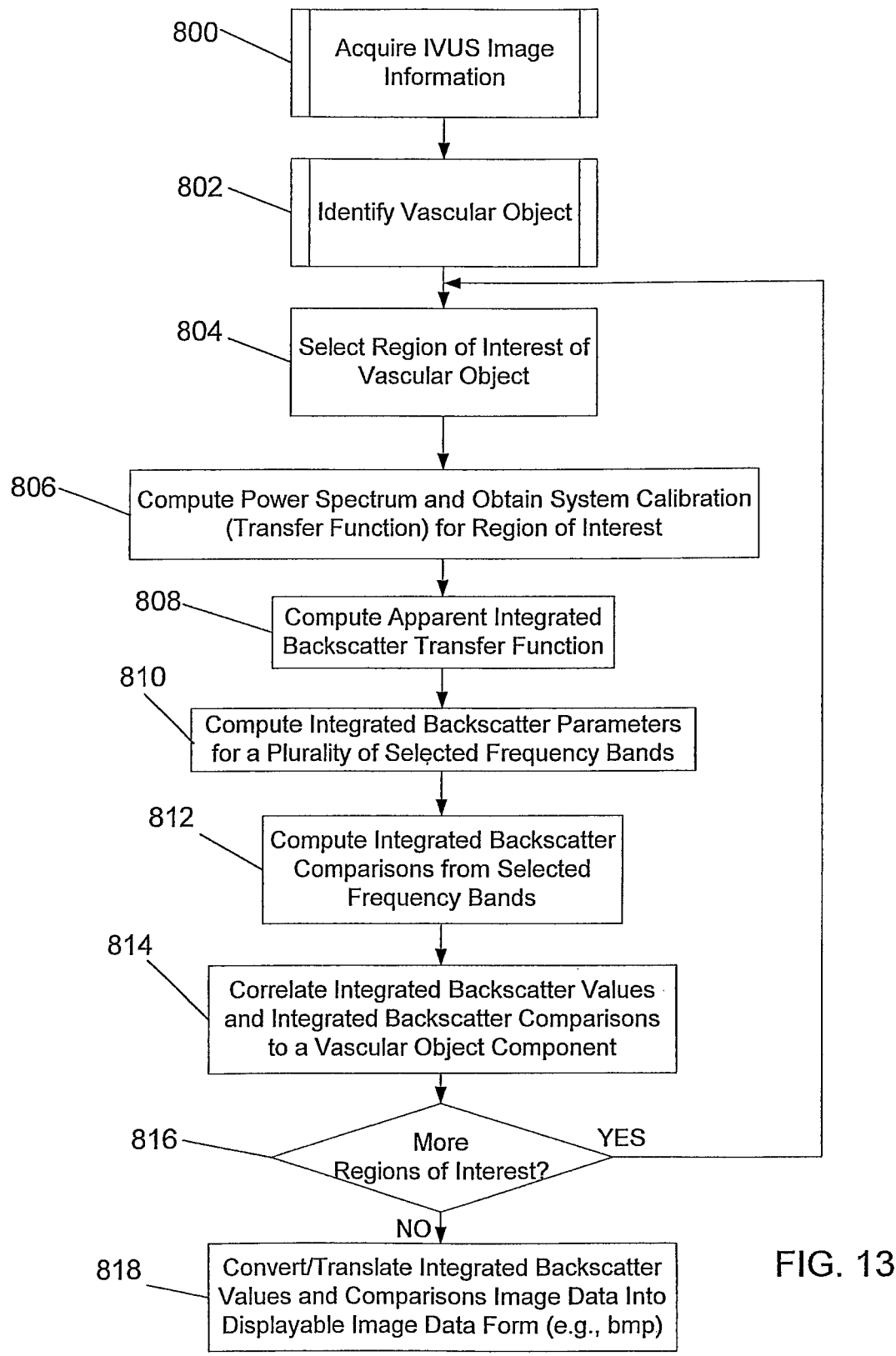
FIG. 13 is a flowchart summarizing an exemplary set of steps for generating integrated backscatter information to generate plaque tissue characterization data in accordance with an illustrative embodiment.

Turning now to FIG. 13, a flowchart summarizes a set of steps wherein the above-calculated transfer function is applied to render integrated backscatter information to generate plaque tissue characterization data in accordance with an illustrative embodiment. During step 800 the tissue characterization application acquires raw IVUS image data. Next, at step 802 a vascular object is identified by a user. Thereafter, at step 804 the user selects a region of interest within an imaging probes' present field of view.

At step 806, the system independently computes the power spectrum for an echo signal segment and obtains the system calibration information applicable to the selected region of interest. Such calibration information includes, but is not limited to the point spread function and/or system transfer function (see, FIG. 7 described herein above). The point spread function is the spatial (or temporal) domain version of the system transfer function, and is related to the system's impulse response. The point spread function calculated, for example, from the system transfer function by Fourier analysis.

Thereafter, at steps 808 and 810 the system calculates the ABSTF (808) and IB parameters at multiple sub-bands (810) for the selected region of interest. During step 812, in an exemplary embodiment a low and high sub-band IB are compared to render a signed difference signal (as opposed to an unsigned magnitude value) that potentially aids correlating a signal's parameter value with a particular tissue characterization.

Next, during step 814 the values computed during steps 810 and 812 are applied to characterization criteria to render a tissue characterization. If additional regions of interest exist, then control passes from step 816 back to step 804. Otherwise, at step 818 the designated characterizations for the various regions of interest are combined into a single displayed image according to the assigned tissue characterizations.

The IB parameters calculated within two or more bands of a larger spectral band, by a system embodying the aforementioned ultrasound echo parameterization scheme, are used as input to a tissue characterization application that utilizes parametric data provided by potentially many sources to render a tissue type corresponding to an ultrasound echo segment. An example of such system is described, by way of example, in Nair et al., U.S. application Ser. No. 11/689,327.

The tissue characterization output of the above-described system is thereafter used, by way of example, to provide input to a system for classifying vascular plaque lesions wherein a classification criterion is applied by a plaque classification application to at least one graphical image of a cross-sectional slice of a vessel to render an overall plaque classification for the slice or set of slices, covering a 3D volume. Such system is described, by way of example, in Margolis et al., U.S. application Ser. No. 11/689,963 (now US Pub. App. 2007/0260141.

It is noted that while the illustrative embodiment discloses the use of two frequency bands, in alternative embodiments more bands are used. Furthermore, the multiple bands may overlap or have band gaps between them.

Systems and their associated components and/or methods have been described herein above with reference to exemplary embodiments of the invention including their structures and techniques. It is noted that the present invention is implemented in computer hardware, firmware, and software in the form of computer-readable media including computer-executable instructions for carrying out the described functionality/methodology. In view of the many possible embodiments to which the principles of this invention may be applied, it should be recognized that the embodiments described herein with respect to the drawing figures are meant to be illustrative only and should not be taken as limiting the scope of invention. Therefore, the invention as described herein contemplates all such embodiments as may come within the scope of the following claims and equivalents thereof.

What is claimed is:

1. A method of evaluating vascular tissue, comprising:
   inserting at least a portion of an intravascular device into a vascular structure;
   activating an ultrasound transducer of the intravascular device, wherein activating the ultrasound transducer results in an ultrasound signal being transmitted toward vascular tissue of the vascular structure;
   acquiring a scan line of backscattered ultrasound data from the vascular tissue;
   applying a one-dimensional homomorphic deconvolution operation to digital data corresponding to the scan line of backscattered ultrasound data to render an estimated scan-line system transfer function; and
   calculating ultrasound response data for the vascular tissue based upon the estimated scan-line system transfer function.

2. The method of claim 1, wherein calculating the ultrasound response data for the vascular tissue includes using a system transfer function that is based upon the estimated scan-line system transfer function.

3. The method of claim 2, wherein the acquiring step and the applying step are performed multiple times to render a plurality of estimated scan-line system transfer functions within a single image frame, and the system transfer function is an average of the plurality of estimated scan-line system transfer functions within the single image frame.

4. The method of claim 2, wherein calculating the ultrasound response data for the vascular tissue includes calculating an apparent backscatter transfer function (ABSTF) by deconvolving the system transfer function from a power spectrum of ultrasound data corresponding to points within a region of interest within the vascular structure.

5. The method of claim 2, wherein the system transfer function is rendered in the form of a power spectrum.

6. The method of claim 1, wherein the applying step comprises calculating a power cepstrum of the digital data corresponding to the scan line of backscattered ultrasound data.

7. The method of claim 6, wherein the applying step comprises applying a filter to the power cepstrum of the digital data corresponding to the scan line of backscattered ultrasound data to render a cepstral point spread function on the scan line.

8. The method of claim 7, wherein the filter is a low pass filter.

9. The method of claim 7, wherein the applying step further comprises generating a system transfer function amplitude spectrum by taking an exponential of a Fourier transform of the cepstral point spread function on the scan line.

10. The method of claim 9, wherein the applying step comprises generating a system power transfer function by taking the square of absolute values of the system transfer function amplitude spectrum on the scan line.

11. A system for evaluating vascular tissue, comprising:
    a control system configured to interface with an intravascular device sized and shaped for insertion into a vascular structure such that the control system acquires a scan line of backscattered ultrasound data representative of vascular tissue of the vascular structure from the intravascular device while the intravascular device is positioned within the vascular structure, the control system including a processor configured to:
    apply a one-dimensional homomorphic deconvolution operation to digital data corresponding to the scan line of backscattered ultrasound data to render an estimated scan-line system transfer function; and
    calculate ultrasound response data for the vascular tissue based upon the estimated scan-line system transfer function.

12. The system of claim 11, wherein the processor is configured to calculate the ultrasound response data for the vascular tissue by using a system transfer function that is based upon the estimated scan-line system transfer function.

13. The system of claim 12, wherein the processor is configured to calculate the system transfer function as an average of a plurality of estimated scan-line system transfer functions of a single image frame.

14. The system of claim 12, wherein the processor is configured to calculate the ultrasound response data for the vascular tissue by calculating an apparent backscatter transfer function (ABSTF) by deconvolving the system transfer function from a power spectrum of ultrasound data corresponding to points within a region of interest within the vascular structure.

15. The system of claim 12, wherein the processor is configured to render the system transfer function in the form of a power spectrum.

16. The system of claim 11, wherein the processor is configured to apply the one-dimensional homomorphic deconvolution operation by calculating a power cepstrum of the digital data corresponding to the scan line of backscattered ultrasound data.

17. The system of claim 16, wherein the processor is configured to apply the one-dimensional homomorphic deconvolution operation by applying a filter to the power cepstrum of the digital data corresponding to the scan line of backscattered ultrasound data to render a cepstral point spread function on the scan line.

18. The system of claim 17, wherein the filter is a low pass filter.

19. The system of claim 17, wherein the processor is configured to apply the one-dimensional homomorphic deconvolution operation by generating a system transfer function amplitude spectrum by taking an exponential of a Fourier transform of the cepstral point spread function on the scan line.

20. The system of claim 19, wherein the processor is configured to apply the one-dimensional homomorphic deconvolution operation by generating a system power transfer function by taking the square of absolute values of the system transfer function amplitude spectrum on the scan line.

* * * * *